United States Patent [19]
Taupier et al.

[11] Patent Number: 4,816,401
[45] Date of Patent: Mar. 28, 1989

[54] SERUM FREE CELL CULTURE MEDIUM

[75] Inventors: Mary A. Taupier; Edith M. Lord, both of Rochester, N.Y.

[73] Assignee: University of Rochester, Rochester, N.Y.

[21] Appl. No.: 774,114

[22] Filed: Sep. 9, 1985

[51] Int. Cl.$^4$ .............................................. C12N 5/00
[52] U.S. Cl. .......................... 435/240.31; 435/240.3; 435/240.2; 435/240.1
[58] Field of Search ................. 435/240, 241, 948, 68, 435/240.2, 948, 68, 240.3, 240.31

[56] References Cited

U.S. PATENT DOCUMENTS

| | | | |
|---|---|---|---|
| 4,636,463 | 1/1987 | Altman et al. | 435/7 |
| 4,652,522 | 3/1987 | Kennett et al. | 435/68 |
| 4,673,649 | 6/1987 | Boyce et al. | 435/240 |

OTHER PUBLICATIONS

Kovar, J. et al. (1984), Immunol. Lett. 7, 339–345.
Gibco catalog, p. 185 (1985).
Iscove, N. N.: Culture of Lymphocytes and Hemopoietic Cells ..., in Methods for Serum-Free Culture ... (1984).
Darfler, F. J. et al.: Growth of Lymphoid Cells ..., in Methods for Serum-Free Culture ... (1984).
Murakami, H.: Serum-Free Cultivation of Plasmacytomas ... in Methods for Serum-Free Culture ... (1984).
Mendelsohn, J. et al.: Culture of Human Lymphocytes ..., in Methods for Serum-Free Culture ... (1984).
Murakami, H. et al.: Growth of Hybridoma Cells in Serum-Free ..., PNAS 79: 1158 (1982).
Bottenstein, J. et al.: The Growth of Cells in Serum--Free ..., Basic Methods of ... (1979).
Kawamoto, T. et al.: Development of a Serum-Free Medium ..., Anal. Biochem. 130: 445 (1983).
Bettger, W. J. et al.: The Critical Role of Lipids ..., in Growth of Cells in Hormonally ... (1982).
Spieker-Polet, H. et al.: Requirement of a Combination of ..., J. Immunol. 126: 949 (1981).
Hammond, S. L. et al.: Serum-Free Growth of Human ..., PNAS 81, 5435 (1984).
Barnes, D. et al.: Serum-Free Cell Culture ..., Cell 22: 649 (1980).
Barnes, D. et al.: Methods for Growth of Cultured Cells ..., Anal. Biochem. 102: 255 (1980).
Mendelsohn, J. et al.: Proliferation of Normal Human Lymphocytes ..., in Growth of Cells in Hormonally ... (1982).
McHugh, Y. E. et al.: Serum-Free Growth of Murine and Human ..., Biotechniques Jun./Jul. (1983).
Mosier, D. E.: Primary in Vitro Antibody Responses by ..., J. Immunol. 127: 1490 (1981).
Ham, R6: Importance of the Basal Nutrient Medium ..., in Growth of Cells in Hormonally ... (1982).
Hatzfeld, J. et al.: Specific Roles of Lipids, Transferrin ..., in Growth of Cells in Hormonally ... (1982).
Promotional Material for PBM by JR Scientific.
Promotional Material for Ventrex HL-1 by Ventrex Laboratories (1984).
Promotional Material for Opti-MEM by Gibco Laboratories (1985).

Primary Examiner—Thomas G. Wiseman
Assistant Examiner—Patterson, Jr. Charles L.
Attorney, Agent, or Firm—Martin LuKacher

[57] ABSTRACT

A serum free cell culture medium containing less than 10 ug/ml protein is disclosed. The medium comprises a basal media supplemented with levels of 2-aminoethanol substantially higher than previously disclosed and supplemented with 2-mercaptoethanol, transferrin, insulin and free essential amino acids. Unlike other serum free media, the media disclosed herein will support the growth and long term culture of a large variety of cell types including hybridomas and tumor cell lines while maintaining both growth potential and the differentiated characteristics of the particular cell line.

12 Claims, 6 Drawing Sheets

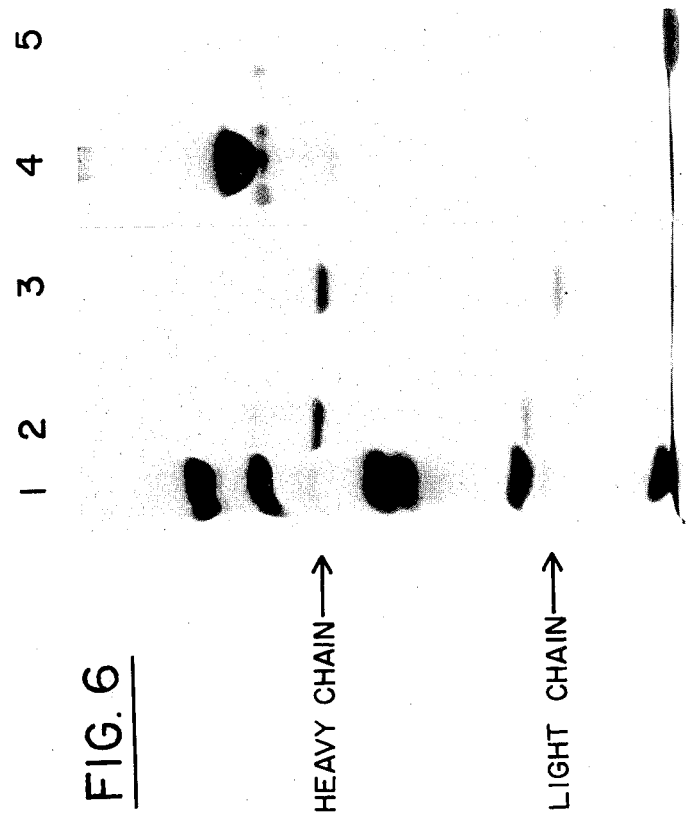

SERUM FREE CELL CULTURE MEDIUM

This invention relates to the field of long term cell culture in serum free very low protein media. It provides for a composition comprising a basal medium supplemented with levels of 2-aminoethanol substantially higher than previously recognized and supplemented with 2-mercaptoethanol, transferrin, insulin, and free essential amino acids. Where the medium is exposed to wavelengths of light of less than 500 nm, a mixture of trace elements or selenium alone is added to the composition.

Since the advent of growth of mammalian cells in culture, efforts have been made to better define the requirements necessary for optimal cell growth. However, traditional supplementation of these media with serum of equine or bovine origin, which contain a myriad of undefined components, has presented complications in many areas of study. For a review of the use of serum free media, see Barnes and Sato.

Recently, however, much effort has been made to overcome these complications by replacing the serum in cell culture media with more defined protein and hormonal mixtures. In hormonal and nutritional studies, it is essential to eliminate undefined or unnecessary components to be able to define the hormonal and nutritional requirements necessary for the growth and activation of cells. In addition, the nutrients required for the growth of neural cells in the absence of serum have been analyzed primarily out of necessity, since traditional serum containing media selectively allow the growth of fibroblastoid cells to the detriment of neural cells.

In order to facilitate monoclonal antibody purification, much work also has been done to develop a serum free medium that will grow hybridoma cells. Unfortunately, most of these media contain quite high levels of exogenous protein necessitating purification steps such as ammonium sulfate precipitation or acid elution from an affinity column, either of which may inactivate some of the antibody desired. In addition, since these media were developed specifically for the culture of hybridoma cells, these formulations often will not grow other types of tumor cells. Those serum free media which have been developed to grow a particular tumor cell will only grow a limited number of other tumor cell types optimally, possibly because they were specifically tailored to the needs of a single cell line.

Recently, both Ziegler and Milstein (1979) and van Agthoven and Terhorst (1982) have reported that a new type of $\beta$-2 microglobulin molecule was associated with murine T cells. Further study however, revealed that this new molecule was bovine $\beta$-2 microglobulin derived from the fetal bovine serum (FBS) that the cells were cultured in. This illustrates the problems in data interpretation that can arise when protein components from the media bind to the membrane or membrane proteins of a cell.

In a similar manner, studies on the immune reactions to activated and tumor cells grown in culture can be complicated by components of FBS adsorbed onto the cells. Many reports have detailed a response to these FBS components rather than to tumor or activation antigens when these cultured cells are subsequently injected into animals. This has resulted in anti-FBS antibodies or polyclonal non-specific cytolytic responses.

To avoid the problems associated with high levels of protein and lipids and those associated with the use of a defined medium incapable of sustaining long-term growth or growth only in a single or limited number of cell lines, a serum free very low protein medium for long term cell culture (MAT/P) is disclosed containing less than 10 ug/ml total protein which will support the growth of a wide variety of cell cultures.

An object of this invention is to allow a wide variety of cell lines to be cultured.

A further object of this invention is to provide a medium which will sustain cell cultures in a manner as near to cell culture in serum as possible.

An advantage of this invention is that the cells can be cultured over a long term.

Another advantage is that the low protein concentration will not mask antigens.

Another advantage is that the low protein concentration will not generate spurious immune responses upon injection into animals.

A further advantage of this invention is that the media is relatively inexpensive compared to media containing serum.

A final advantage is that purification of monoclonal antibodies and biological response modifiers is simplified.

These and other objects and advantages will become apparent from a reading of the following detailed description of the invention and associated Figures in which:

FIG. 1 is a plot of cell growth, as measured by tritiated thymidine, uptake against time for a variety of cell types in several different media wherein media used were: ● RPMI 1640 with $5 \times 10^{-5}$M 2-mercaptoethanol and 10% FBS; ◇ HB101 ® supplemented with sodium pyruvate and glutamine (as recommended by the manufacturer); O Iscove's modified Dulbecco's media:Ham's F12 (IMDM/F12) at a 1:1 ratio; ◆ RPMI 1640:Dulbecco's modified Eagle's media:Ham's F12 (RPMI 1640/DMEM/F12) at a 2:1:1 ratio; △ RPMI 1640; ■ DMEM/F12 at a 1:1 ratio; □ RPMI 1640/IMDM/F12 at a 2:1:1 ratio; O, ◆, △, ■, □ were all supplemented with the trace element mix, and the concentrations of progesterone, insulin, and transferrin described by Mosier (1981), as well as 20 uM 2-aminoethanol;

FIG. 2 is a plot similar to FIG. 1 wherein various substances were tested for their ability to enhance the growth of cells above that found in RPMI/DMEM/F12 supplemented as described in FIG. 1 with vitamins and minimal essential medium amino acids (EAA) used at the concentration recommended by the manufacturer, bovine serum albumin (BSA) used at 500 ug/ml and putrescine used at $5 \times 10^{-5}$M;

FIG. 3 is a plot similar to FIG. 1 wherein transferrin, 2-aminoethanol, and essential amino acids were tested to determine optimal concentrations: A and D) transferrin ● 50 ug/ml, △ 10 ug/ml, □ 2 ug/ml, ◆ none; B and E) 2-aminoethanol ● 900 uM, △ 300 uM, □ 100 uM, ◆ 20 uM; C and F) minimal essential medium amino acids ● 40 ml/L, △ 20 ml/L, □ 10 ml/L, ◆ 5 ml/L;

FIG. 6 is a 10% SDS-PAGE analysis of the results of concentrating hybridoma supernatants grown in MAT/P, over a 100,000 MW cut-off filter in a Millipore Minitan ®.

In order to deplete FBS components, cell lines EMT6.S, EMT6.R.1, YAC-1, Line 1, RIF-1, and the hybridoma M1/70.15.11.5 were grown for at least four passages in Mosier's modification of Iscove's medium further supplemented with 20 uM 2-aminoethanol. The growth of some of these cell lines, especially YAC-1, M1/70, and RIF-1 was clearly sub-optimal in that the doubling time was much longer, and the cells had to be passed at a much higher density than was usual in FBS containing media. In addition, about 2-3 days after the initial passage into serum free media a greater lag was often noticed in cell doubling time by microscopic examination, possibly due to depletion of FBS components carried over on the surface of the cells. Therefore, a better basal media to grow this variety of tumor cells was sought. A variety of basal media were tested with the results presented in FIG. 1.

In some cases several of the serum free formulations were quite similar in their ability to support the growth of one cell line and yet distinct differences were seen with the same formulations on other cell lines (e.g., RPMI/IMDM/F12 and RPMI both support the growth of EMT6.S.R.1 to a similar extent, however, only RPMI/IMDM/F12 and not RPMI will support the growth of YAC-1). Since the requirement is for a media that would grow all of these tumor cells, RPMI/DMEM/F12 was chosen as the basal media.

Others have reported that supplementation of serum free media with BSA, lipid-protein extracts, other proteins, nutrients, or hormones were necessary to grow various types of cells in serum free media. The next step was to determine what the effect of these additives would be on the cell lines under study. EMT6.S, YAC-1 and M1/70 were chosen as representative cell lines.

Figure 1:
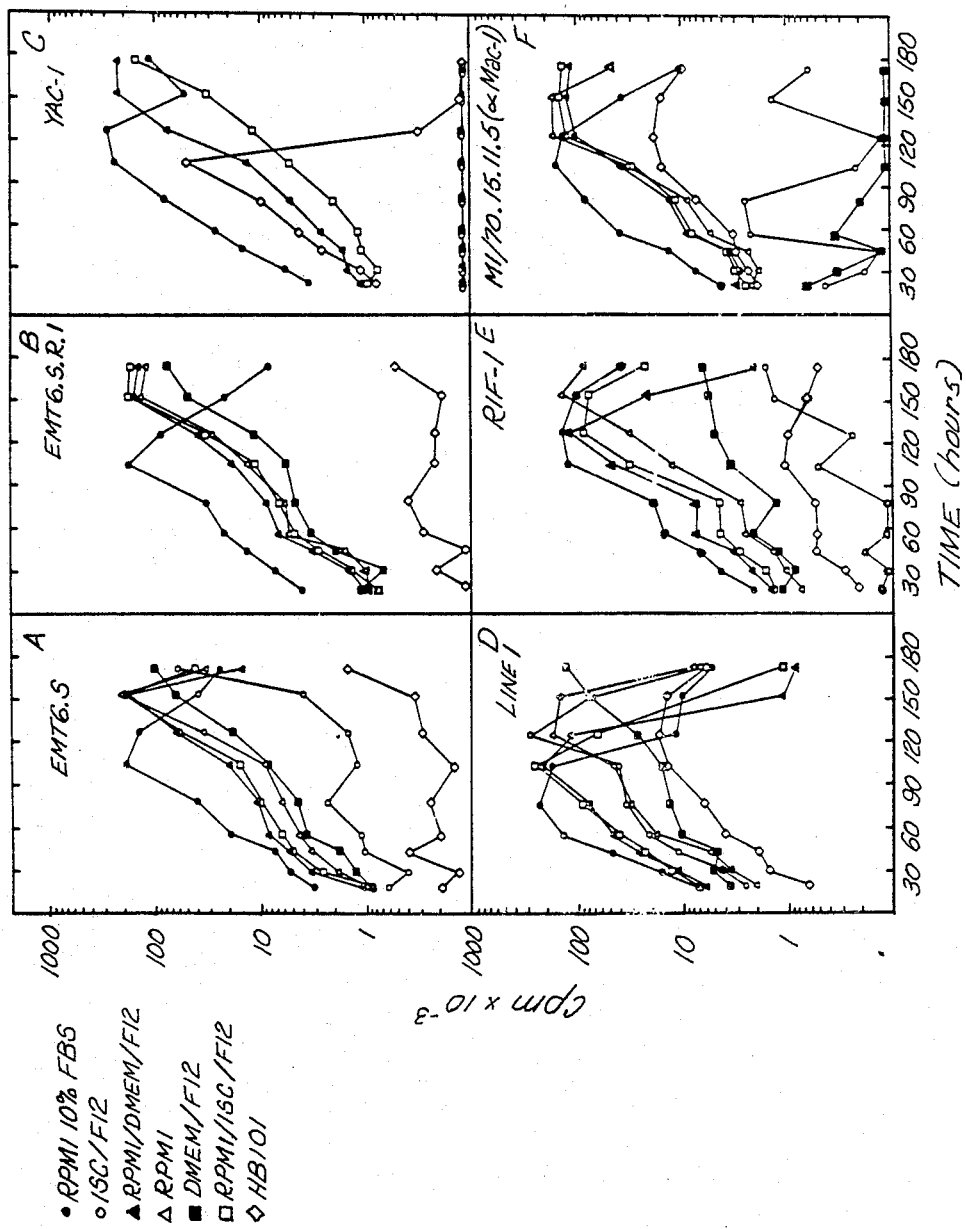
Figure 2:
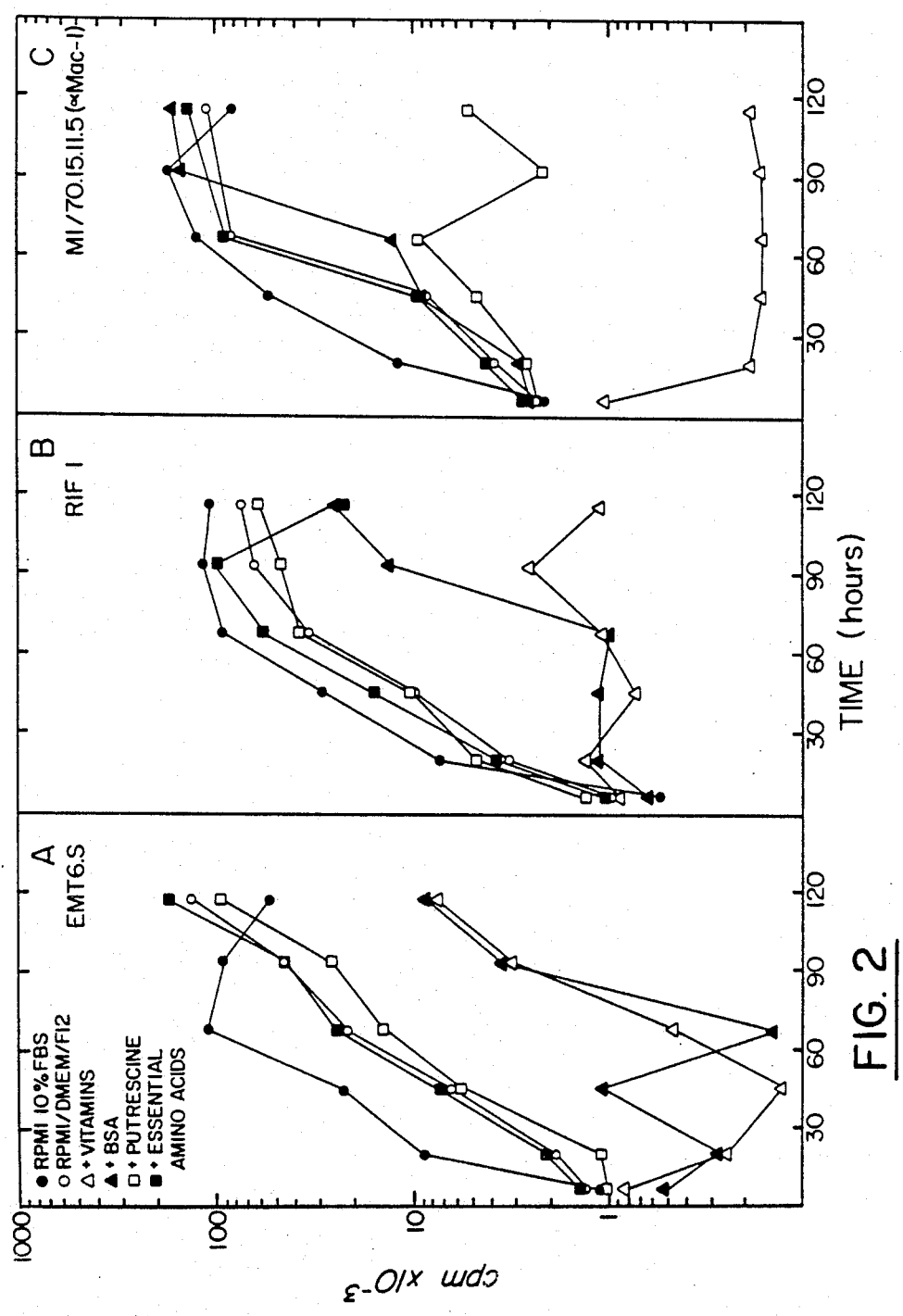

Cells that were in log phase, and growing in RPMI/DMEM/F12 plus the additives described in FIG. 1 for at least 3 passages, were placed in media containing these other additives. See FIG. 2. The control cells, assayed in RPMI with 10% FBS were continually passaged in 10% FBS, since it became apparent that as the cells became fully adapted to serum free media they required a re-adaptation to serum containing media before optimal growth was achieved. To minimize the possibility of divergence in growth characteristics between the cultures being maintained in medium containing serum versus serum-free media, the serum free cultures were only assayed between four and ten passages out of serum.

The effects of these additives fall into several categories. See FIG. 2. First, additives that have little or no effect on one cell line but are somewhat helpful to another (i.e., essential amino acids). Second, additives which appear to be detrimental to several cell lines. These are BSA especially in the case of EMT6.S and RIF-1. While putrescine had little effect on EMT6.S or YAC-1, it was somewhat toxic to M1/70, and therefore, no additional putrescine was added the formulation. Other compounds tested and found to have no effect or to be toxic were catalase, alpha cyclodextrin, dexamethasone, sodium pyruvate, non-essential amino acids and progesterone. No additives were tested that were beneficial to one cell line and detrimental to another.

Figure 3:
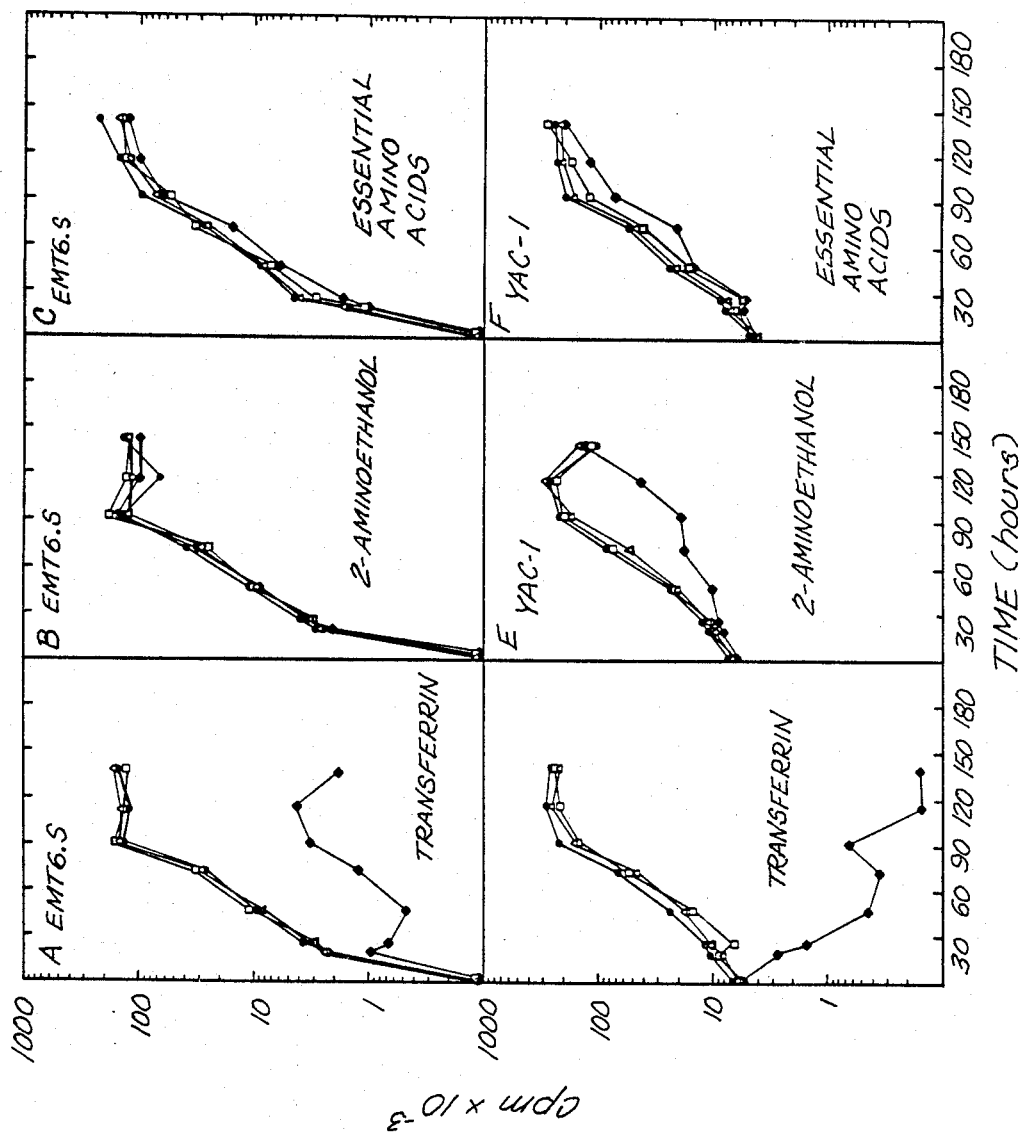

Once the necessary additives were established, 2-aminoethanol, transferrin, minimal essential medium amino acids, and insulin were then titrated on EMT6.S and YAC-1 to determine the optimal concentrations for cell growth. FIG. 3 shows the results of these experiments.

Both cell lines show an absolute requirement for ⅓ iron saturated transferrin. However, both cell lines did well whether the concentration was 2 ug/ml or 50 ug/ml. 2 ug/ml has been chosen as the preferred concentration in order to minimize protein content in the medium.

While EMT6.S shows no significant difference in its requirements for 2-aminoethanol, YAC-1 grew poorly when the concentration dropped below 100 uM. The optimal range is from 400–800 uM with a preferred concentration of 600 uM. The toxicity of 2-aminoethanol reported by Murakami, et al. (1982) at levels of greater than 20 uM was not seen in concentrations as high as 1200 uM.

Insulin worked well in both cell lines regardless of whether the concentration was 2 ug/ml or 20 ug/ml.

Figure 4:
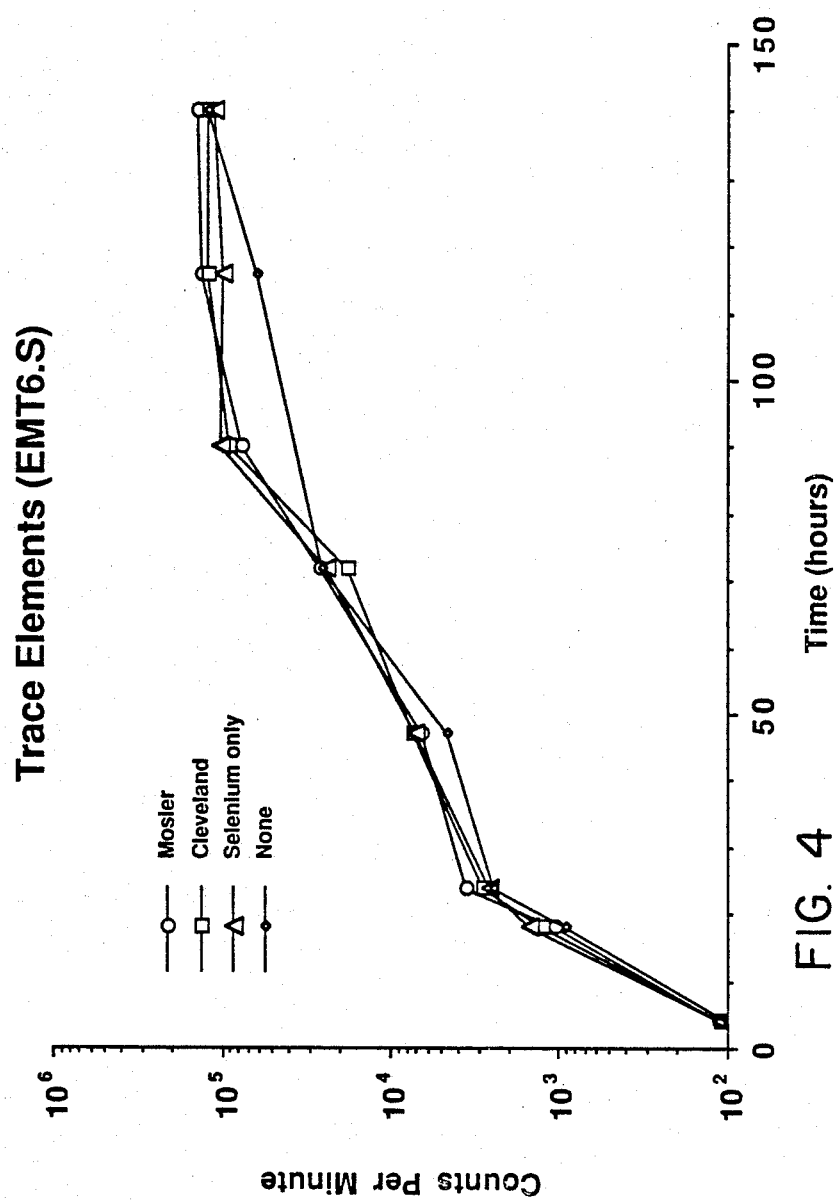
FIG. 4 is a plot similar to FIG. 3 wherein various trace element mixtures were tested on cell lines EMT6.S and YAC-1:O trace element mix described by Mosier (1981), □ trace element mix described by Cleveland (1983), △ $2 \times 10^{-8}$M Na$_2$SeO$_3$ only; or ◇ no trace elements.

The highest level of essential amino acids (i.e., 40 ml/L) consistently, although not significantly, augmented the growth of EMT6.S and had a greater effect on YAC-1. Two trace element mixes, selenium alone or no trace elements also were tested. As can be seen in FIG. 4, all three selenium containing mixes worked approximately the same for both EMT6.S and YAC-1. What was surprising, however, was that the absolute requirement for selenium to grow cells in serum free media reported by others, and seen in preliminary experiments done with EMT6.S, was no longer present for either EMT6.S or YAC-1. Since selenium is a cofactor for peroxidase, it may have been due to elimination of phototoxic products in the media by eliminating wavelengths of less than 500 nM. Using the media described above, selenium and other trace elements are not necessary to grow the cell lines described for short periods of time but Mosier's trace element mixture has been retained in the formulation since it does appear to be helpful in long term culture.

Given these results, the following preferred embodiment was derived. Glutamine free RMPI 1640 is combined 2:1:1 with glutamine free Dulbecco's modified Eagle's medium and Ham's F12. To this is added 40 ml/L of minimal essential media amino acids and either Mosier's trace element mixture or $2 \times 10^{-8}$M $Na_2SeO_3$. 1.6 gm/L of $NaHCO_3$ is added and the pH is adjusted to 7.2. At this point the medium is sterilized by filtration and may be stored in the dark at 4° C. for up to 2 months.

At the time of use, 600 uM 2-aminoethanol, 50 uM 2-mercaptoethanol, 332.5 mg/L L-glutamine, 5 ug/ml insulin and 2–10 ug/ml one third iron saturated transferrin are added. The medium is buffered to be used in a 5% $CO_2$ culture conditions. Table I provides a complete breakdown of all the components of MAT/P.

TABLE I

| MAT/P:Formulation | |
| --- | --- |
| | mg/liter |
| Salts | |
| $Ca(No_3)_2.4H_2O$ | 50. |
| $CaCl_2$ | 58.3 |
| $Fe(No_3)_3.9H_2O$ | 0.25 |

TABLE I-continued

MAT/P:Formulation

| Component | mg/liter |
|---|---|
| KCl | 355.9 |
| MgSO$_4$ (Anhydrous) | 48.84 |
| NaCl | 6497.975 |
| NaHCO$_3$ | 1600. |
| NaH$_2$PO$_4$ (Anhydrous) | 31.25 |
| CuSO$_4$.5H$_2$O | 0.00065 |
| FeSO$_4$.7H$_2$O | 0.2085 |
| MgCl$_2$ | 14.32 |
| Na$_2$HPO$_4$ | 435.51 |
| ZnSO$_4$.7H$_2$O | 0.216 |
| Other Components | |
| Sodium Hypoxanthine | 1.195 |
| Linoleic Acid | 0.021 |
| D-glucose | 2575.5 |
| Lipoic Acid | 0.0525 |
| Putrescine.2HCl | 0.0405 |
| Thymidine | 0.1825 |
| Phenol red | 6.55 |
| DL-Thioetic acid | 0.525 |
| Glutathione (reduced) | 0.5 |
| HEPES | 1787.25 |
| Sodium Pyruvate | 27.5 |
| Amino Acids | |
| L-Alanine | 2.225 |
| L-Asparagine | 25. |
| L-Asparagine.H$_2$O | 3.75 |
| L-Arginine free base | 100. |
| L-Arginine.HCl | 326.55 |
| L-Aspartic Acid | 13.325 |
| L-Cysteine.HCl.H$_2$O | 8.78 |
| L-Cystine | 48. |
| L-Cystine.2HCl | 48.22 |
| L-Glutamic Acid | 13.675 |
| Glycine | 14.375 |
| L-Histidine (free base) | 7.5 |
| L-Histidine.HCl.H$_2$O | 99.74 |
| L-Hydroxyproline | 10. |
| L-Isoleucine | 157.235 |
| L-Leucine | 159.325 |
| L-Lysine.HCl | 210.625 |
| L-Methionine | 46.325 |
| L-Phenylalanine | 91.24 |
| L-Proline | 18.625 |
| L-Serine | 28.125 |
| L-Threonine | 131.925 |
| L-Tryptophan | 27.41 |
| L-Tyrosine | 72. |
| L-Tyrosine.2Na | 14.415 |
| L-Tyrosine.2Na.2H$_2$O | 27.875 |
| L-Valine | 130.025 |
| Vitamins | |
| Biotin | 0.10175 |
| D-calcium pantothenate | 1.245 |
| Choline Chloride | 5.99 |
| Folic Acid | 1.825 |
| i-Inositol | 23.8 |
| Nicotinamide | 0.5 |
| Para-aminobenzoic acid | 0.5 |
| Pyridoxine.HCl | 0.5155 |
| Riboflavin | 0.2095 |
| Thiamine.HCl | 1.585 |
| Vitamin B12 | 0.3425 |
| Niacinamide | 1.01 |
| Pyridoxal.HCl | 1.0 |
| Trace Elements | |
| MnCl$_2$ | 0.5 nM |
| (NH$_4$)$_6$Mo$_7$O$_{24}$ | 0.5 nM |
| NiSO$_4$ | 0.25 nM |
| H$_2$SeO$_3$ | 15. nM |
| Na$_2$SeO$_3$ | 50. nM |
| Na$_2$SiO$_3$ | 250. nM |
| SnCl$_2$ | 0.25 nM |
| NaVO$_3$ | 2.5 nM |
| CdSO$_4$ | 50. nM |
| Added at Time of Use - Unstable Components | |
| L-Glutamine | 332.5 mg/L |
| 2-mercaptoethanol | $5 \times 10^{-5}$ μM |
| 2-aminoethanol (ethanolamine) | 600 uM |
| Transferrin | 1 to 5 mg/L |
| Insulin | 5 mg/L |

In this state, MAT/P has a shelf life of 3 weeks when stored in the dark at 4° C. Without the materials added at the time of use, shelf life is 2 months when stored in the dark at 4° C.

Figure 5:
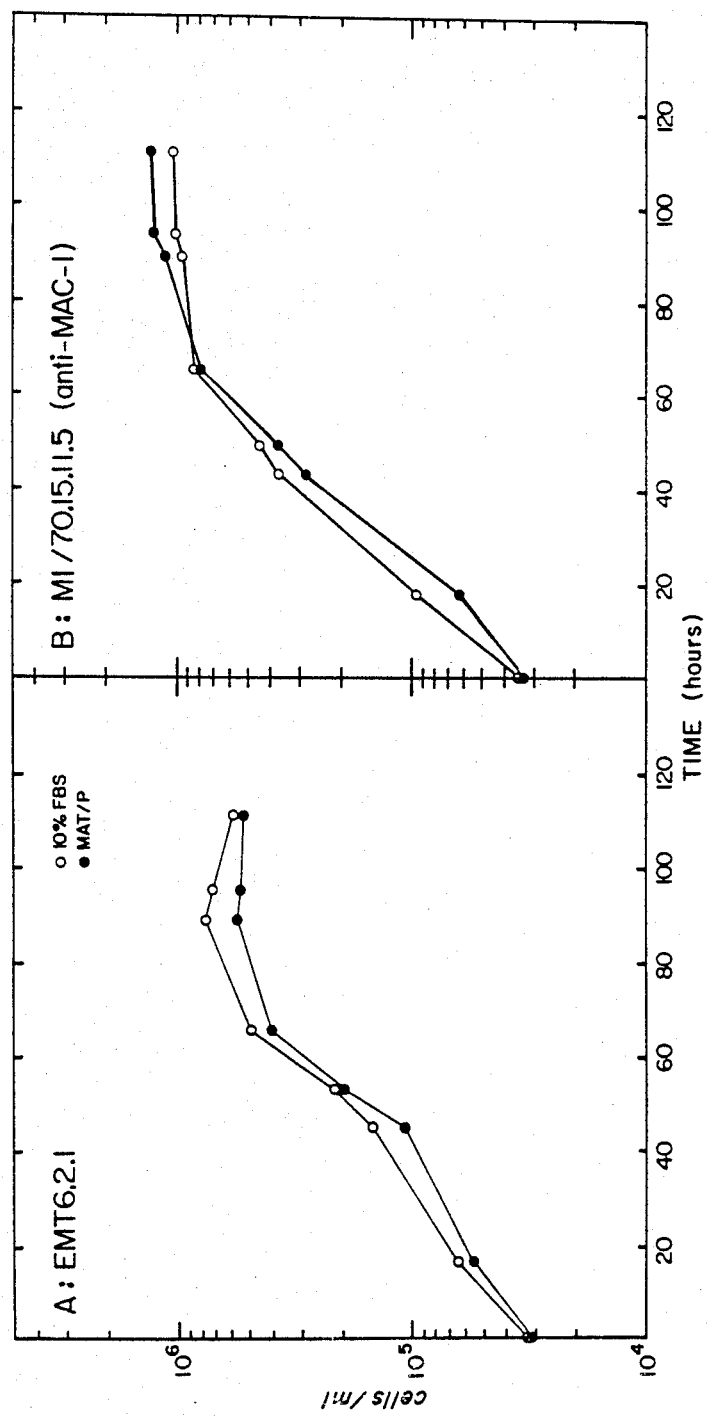
FIG. 5 is a plot of cell concentration against time wherein EMT6.S and M1/70 were tested for growth in MAT/P vs. RPMI 1640 with 10% FBS and 2-mercaptoethanol.

Growth then was tested for in MAT/P. FIG. 5 shows that the growth kinetics of EMT6.S and M1/70 are the same in RPMI containing 10% FBS as in MAT/P. EMT6.S, M1/70, YAC-1, RIF-1 and Line 1 have since been continuously cultured for up to five months in this formulation, with no changes in growth or other characteristics.

To determine the breadth of use of MAT/P, cell lines were tested for long term growth. Table II illustrates the variety of cells isolated from mouse, rat and human that have been tested and will grow in MAT/P. Most importantly, as well as supporting the growth of these cells, MAT/P also supports differentiated functions (e.g., secretion of monoclonal antibody by hybridoma cells). In addition, the immunosuppressive factor produced by the parental EMT6.S line and some of the subclones of EMT6.is still produced at similar levels in MAT/P as in serum containing media. Other cellular characteristics such as response to stimuli are maintained (e.g., Line 1 expresses similar levels of H-2 antigen when cultured in the presence of DMSO in serum containing medium or in MAT/P; PC 12 responds to neural growth factor in serum containing media or MAT/P).

TABLE II

CELL LINES THAT HAVE THE SAME GROWTH CHARACTERISTICS IN MAT/P AS IN FBS CONTAINING MEDIA:

| Cell Line | Origin | Length of Time Cultured |
|---|---|---|
| Sarcomas (adherent) | | |
| EMT6.S/Ro & sublcones .2.1 .8 .R.1 .P | BALB/c spontaneous mammary sarcoma(g) (secretes immunosuppressive factor in MAT/P as in FBS) each clone has differing growth characteristics which are maintained in MAT/P | 6 months |
| Line 1 | BALB/c spontaneous lung tumor(h) (Expresses H$_2$ in response to DMSO in MAT/P as in FBS). | 6 months |
| Meth A.4 | Methyl-cholanthrene induced sarcoma(i) (non-adherent variant) of BALB/c mice | 2 months |
| RIF-1 | C3H radiation induced fibrosarcoma(j) | 6 months |
| WEHI 164 | NC susceptible cell line of BALB/c mice(k) | 4 months |
| Hybridoma Lines | | |

TABLE II-continued
CELL LINES THAT HAVE THE SAME GROWTH CHARACTERISTICS IN MAT/P AS IN FBS CONTAINING MEDIA:

| Cell Line | Origin | Length of Time Cultured |
|---|---|---|
| M1/70.15.11.5 (anti-MAC-1) | NS-1/rat spleen(a) | 4 months |
| GK1.5 (anti-L3/T4) | SP2-0/rat spleen(b) | 3 months |
| AF3-12.1 (anti-H-2K$^K$) | SP2-0/BALB/c spleen(c) | 3 months |
| 53-6 (anti-Lyt 2) | NS-1/rat spleen(d) | 2 months |
| T24/4017 (anti-Thy1) | S194/5/Lewis rat spleen(e) | 3 months |
| MK-D6 (anti Ia$^K$) | P3X63/(C57B1/6xA/J)F$_1$(f) | 3 months |
| AF4-62.4 (anti-H-2D$^D$) | SP2-0/C3H(c) | 4 months |
| OR-689.2.4 (anti-opiate receptor) | P3/BALB/c spleen(r) | 9 months |
| *Lymphomas* | | |
| YAC-1 | A/Sn T-cell lymphoma(1) | 6 months |
| EL4 | C57BL/6 T-cell lymphoma(m) | 4 months |
| S49.1 | T cell lymphoma(n) | 1 month |
| P815 | DBA/2 Mastocytoma(o) | 6 months |
| *Other Tumor Cell Lines* | | |
| NG108-15 | Rat Neuroblastoma/glioma fusion(p) | 1 month |
| PC12 | Rat pheochromocytoma(q) (chromaffin tumor) (differentiates in presence of NGF in MAT/P as in FBS containing media) | 1 month |
| *Human Cell Lines* | | |
| HT 1080 | Human Colon cancer | 2 weeks |

Note:
Cultures were terminated at the times specified due to experimental design rather than loss of growth potential.

In addition, primary cultures were tested for growth in MAT/P. Five-day cultures of mice spleen cells were found to proliferate in response to concanavalin A or tumor antigens. Culture in this medium of spleen cells from mice immunized to tumor antigens also allowed the generation of specific cytolytic T cells.

Finally, an advantage of having very low amounts of exogenous protein in the media is the ease of purification of secreted products. This is illustrated by FIG. 6. Hybridoma supernatant was concentrated forty fold over a 100,000 m.w. cut-off filter on a Millipore Minitan. The concentrate was assayed for purity by SDS poly-acrylamide gel electrophoresis. Lane 4 contains the transferrin control, lane 5 the insulin control and lanes 1 and 6 are molecular weight standards. The hybridoma supernatants in lanes 2 and 3 yielded two major peaks representing heavy and light chains. No detectable insulin was found retained in either preparation. Although a small amount of transferrin was detected in the GK1.5 hydridoma supernatant, the preparation was still 80 to 90% immunoglobulin as judged by molecular weight. This low protein content has also been useful in not only purifying but also characterizing poorly defined biological response modifiers such as the immunosuppressive factor secreted by EMT6.S.

The examples provided herein are for purposes of explanation only and should not be taken in any limiting sense. Variations and modifications, therefore, of the above-described invention may suggest themselves to those skilled in the art within the scope of this invention.

We claim:

1. A serum-free culture composition containing less than 10 μg/ml of protein comprising a basal medium supplemented with a solution of 2-aminoethanol to a concentration of at least 100 μM, a solution of 2-mercaptoethanol, a solution of transferrin, a solution of insulin and an added solution of essential amino acids.

2. The composition as set forth in claim 1 wherein the basal media comprises a 2:1:1 ratio mixture of RPMI 1640:Dulbecco's modified Eagle's Medium:Ham's F12.

3. The composition as set forth in claim 1 wherein the 2-aminoethanol concentration is 600 μM.

4. The composition as set forth in claim 1 wherein the 2-mercaptoethanol concentration is 50 μM.

5. The composition as set forth in claim 1 wherein the transferrin concentration is 1 to 5 μg/ml of one-third iron saturated transferrin.

6. The composition as set forth in claim 1 wherein the insulin concentration is 5 μg/ml.

7. The composition as set forth in claim 6 wherein the trace element solution comprises a trace element mixture of compounds of Mn, Mo, Ni, Se, Si, Sn, V and Cd.

8. The composition as set forth in claim 7 wherein the selenium comprises $2 \times 10^{-8}$M Na$_2$SeO$_3$.

9. The composition as set forth in claim 1 wherein 40 ml/L of minimum essential medium essential amino acids is added.

10. A serum free cell culture composition containing less than 10 ug/ml protein comprising the following compounds in the following proportions:

| | mg/liter |
|---|---|
| Salts | |
| Ca(No$_3$)$_2$.4H$_2$O | 50. |
| CaCl$_2$ | 58.3 |
| Fe(No$_3$)$_3$.9H$_2$O | 0.25 |
| KCl | 355.9 |
| MgSO$_4$ (Anhydrous) | 48.84 |
| NaCl | 6497.975 |
| NaHCO$_3$ | 1600. |
| NaH$_2$PO$_4$ (Anhydrous) | 31.25 |
| CuSO$_4$.5H$_2$O | 0.00065 |
| FeSO$_4$.7H$_2$O | 0.2085 |
| MgCl$_2$ | 14.32 |
| Na$_2$HPO$_4$ | 435.51 |
| ZnSO$_4$.7H$_2$O | 0.216 |
| Other Components | |
| Sodium Hypoxanthine | 1.195 |
| Linoleic Acid | 0.021 |
| D-glucose | 2575.5 |
| Lipoic Acid | 0.0525 |
| Putrescine.2HCl | 0.0405 |
| Thymidine | 0.1825 |
| Phenol red | 6.55 |
| DL-Thioetic acid | 0.525 |
| Glutathione (reduced) | 0.5 |
| HEPES | 1787.25 |
| Sodium Pyruvate | 27.5 |

| | mg/liter |
|---|---|
| Amino Acids | |
| L-Alanine | 2.225 |
| L-Asparagine | 25. |
| L-Asparagine.H$_2$O | 3.75 |
| L-Arginine free base | 100. |
| L-Arginine.HCl | 326.55 |
| L-Aspartic Acid | 13.325 |
| L-Cysteine.HCl.H$_2$O | 8.78 |
| L-Cystine | 48. |
| L-Cystine.2HCl | 48.22 |
| L-Glutamic Acid | 13.675 |
| Glycine | 14.375 |
| L-Histidine (free base) | 7.5 |
| L-Histidine.HCl.H$_2$O | 99.74 |
| L-Hydroxyproline | 10. |
| L-Isoleucine | 157.235 |
| L-Leucine | 159.325 |
| L-Lysine.HCl | 210.625 |
| L-Methionine | 46.325 |
| L-Phenylalanine | 91.24 |
| L-Proline | 18.625 |
| L-Serine | 28.125 |
| L-Threonine | 131.925 |
| L-Tryptophan | 27.41 |
| L-Tyrosine | 72. |
| L-Tyrosine.2Na | 14.415 |
| L-Tyrosine.2Na.2H$_2$O | 27.895 |
| L-Valine | 130.025 |
| Vitamins | |
| Biotin | 0.10175 |
| D-calcium pantothenate | 1.245 |
| Choline Chloride | 5.99 |
| Folic Acid | 1.825 |
| i-Inositol | 23.8 |
| Nicotinamide | 0.5 |
| Para-aminobenzoic acid | 0.5 |
| Pyridoxine.HCl | 0.5155 |
| Riboflavin | 0.2095 |
| Thiamine.HCl | 1.585 |
| Vitamin B12 | 0.3425 |
| Niacinamide | 1.01 |
| Pyridoxal.HCl | 1.0 |
| Trace Elements | |
| MnCl$_2$ | 0.5 nM |
| (NH$_4$)$_6$Mo$_7$O$_{24}$ | 0.5 nM |
| NiSO$_4$ | 0.25 nM |
| H$_2$SeO$_3$ | 15. nM |
| Na$_2$SeO$_3$ | 50. nM |
| Na$_2$SiO$_3$ | 250. nM |
| SnCl$_2$ | 0.25 nM |
| NaVO$_3$ | 2.5 nM |
| CdSO$_4$ | 50. nM |
| Added at Time of Use - Unstable Components | |
| L-Glutamine | 332.5 mg/L |
| 2-mercaptoethanol | $5 \times 10^{-5}$ μM |
| 2-aminoethanol (ethanolamine) | 600 uM |
| Transferrin | 1 to 5 mg/L |
| Insulin | 5 mg/L |

11. A composition as set forth in claim 1 wherein the concentration of 2-aminoethanol is 400 to 800 μm.

12. A composition as set forth in claim 1 which is also supplemented with a selenium-containing solution of trace elements or with a solution of selenium.

* * * * *